United States Patent [19]

Cerf et al.

[11] Patent Number: 5,663,401

[45] Date of Patent: Sep. 2, 1997

[54] PHOSPHORUS- AND SULFUR-CONTAINING ACRYLATES AND METHACRYLATES

[75] Inventors: Martine Cerf, Metz; Jean Luc Mieloszynski, Montigny les Metz; Daniel Paquer, Vandoeuvre, all of France

[73] Assignee: Atochem, Paris La Defense, France

[21] Appl. No.: 369,484

[22] Filed: Jan. 6, 1995

Related U.S. Application Data

[62] Division of Ser. No. 29,288, Mar. 8, 1993, Pat. No. 5,399,733, which is a continuation of Ser. No. 715,197, Jun. 14, 1991, abandoned.

[30] Foreign Application Priority Data

Jun. 14, 1990 [FR] France ................... 90 07439

[51] Int. Cl.⁶ .................................. C07F 9/165
[52] U.S. Cl. .......................... 558/105; 558/104
[58] Field of Search ......................... 558/105, 104

[56] References Cited

U.S. PATENT DOCUMENTS

| | | | |
|---|---|---|---|
| 3,197,405 | 7/1965 | Le Suer | 558/105 |
| 3,654,154 | 4/1972 | Braid | 558/105 |
| 4,016,222 | 4/1977 | Dursch. | |
| 4,041,230 | 8/1977 | Huber. | |
| 4,515,930 | 5/1985 | Omura. | |

FOREIGN PATENT DOCUMENTS

| | | |
|---|---|---|
| 27 24 243 | 5/1977 | Germany. |
| 2003883 | 3/1979 | United Kingdom. |

OTHER PUBLICATIONS

Kosolapoff, G. M. et al, Organic Phosphorous Compounds, Wiley & Sons, 1976, p. 529 (vol. 7).

*Primary Examiner*—Christopher Henderson
*Attorney, Agent, or Firm*—Millen, White, Zelano & Branigan, P.C.

[57] ABSTRACT

Compounds represented by the formulae (I) and (II) in which:

$R^1$=H or $CH_3$;

X=O or S;

$R^2$=$C_{1-12}$ straight-chain or branched alkylene groups, monocyclic or polycyclic cycloalkylene and heterocycloalkylene groups, alkylarylene and arylalkylene groups;

$R^6$=H or $C_{1-12}$ alkyl and aryl radicals;

$R^3$=$C_{1-20}$ alkyl and aryl radicals, —$(CH_2)_pSR^4$ groups where p=integer from 2 to 12 and $R^4$=$C_{1-20}$ alkyl, and

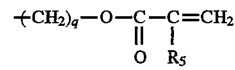

where q is an integer from 2 to 12 and $R^5$=H or $CH_3$.

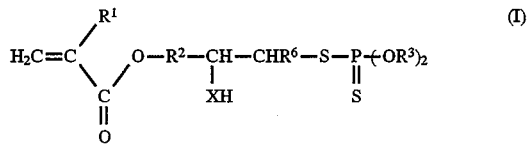

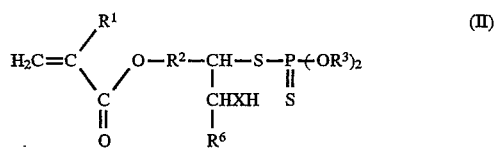

8 Claims, No Drawings

PHOSPHORUS- AND SULFUR-CONTAINING ACRYLATES AND METHACRYLATES

CROSS-REFERENCE TO RELATED APPLICATIONS

This application is a divisional of Ser. No. 08/029,288, now U.S. Pat. No. 5,399,733, which in turn is a continuation of Ser. No. 07/715,197, filed Jun. 14, 1991, now abandoned. In addition, this application is related to application Ser. No. 07/714,180, abandoned in favor of application Ser. No. 07/993,724, now U.S. Pat. No. 5,412,138.

BACKGROUND OF THE INVENTION

The present invention relates to new acrylates and methacrylates containing at least one phosphorus atom and at least one sulfur atom, to a process for preparing them, and to the production of new polymers and copolymers from said acrylates and methacrylates.

Numerous acrylic and methacrylic compounds carrying groups such as halogen, hydroxyl, thiol, epoxide, etc. have already been disclosed in scientific and industrial literature. Each of these groups of compounds has already found varied applications in various industries because of the ease of polymerization of the acrylic double bond. However, to date, scientific and industrial literature has not given examples of acrylic and methacrylic compounds which simultaneously carry at least one phosphorus atom and at least one sulfur atom.

SUMMARY OF THE INVENTION

A first object of the present invention, therefore, relates to acrylic and methacrylic compounds chosen from those of the formula:

$$H_2C=C\begin{matrix}R^1\\ \\C\\ \parallel \\O\end{matrix}O-R^2-CH-CHR^6-S-P(OR^3)_2 \quad (I)$$
$$\quad\quad\quad\quad\quad\quad\quad XH \quad\quad\quad\quad S$$

and those of the formula:

$$H_2C=C\begin{matrix}R^1\\ \\C\\ \parallel \\O\end{matrix}O-R^2-CH-S-P(OR^3)_2 \quad (II)$$
$$\quad\quad\quad\quad\quad\quad CHXH \quad S$$
$$\quad\quad\quad\quad\quad\quad\quad R^6$$

in which formulae:

$R^1$ is a hydrogen atom or a methyl radical;
X is an oxygen or sulfur atom;
$R^2$ is a straight-chain or branched alkylene group, a monocyclic or polycyclic cycloalkylene or heterocycloalkylene group, or an alkylarylene or arylalkylene group comprising from 1 to 12 carbon atoms;
$R^6$ is a hydrogen atom or an alkyl or aryl radical having from 1 to 12 carbon atoms; and
$R^3$ is an alkyl or aryl radical having from 1 to 20 carbon atoms, an —$(CH_2)_pSR^4$ group in which p is an integer ranging from 2 to 12 and $R^4$ is an alkyl radical having from 1 to 20 carbon atoms, or a monocyclic or polycyclic cycloalkyl group having from 4 to 10 carbon atoms, each ring in said group comprising from 4 to 6 members, or a $$\text{—}(CH_2)_q\text{—}O-C-C=CH_2$$
$$\quad\quad\quad\quad\quad \parallel \ \ |$$
$$\quad\quad\quad\quad\quad O \ \ R^5$$

group in which q is an integer ranging from 2 to 12 and $R^5$ is hydrogen or methyl.

A second object of the present invention is a process for preparing acrylic and methacrylic compounds of formula (I), comprising the reaction of an acrylic or methacrylic epoxide or episulfide of the formula $$H_2C=C\begin{matrix}R^1\\ \\C\\ \parallel \\O\end{matrix}O-R^2-CH-CHR^6 \quad (III)$$
$$\quad\quad\quad\quad\quad\quad\quad\quad\quad X$$

in which $R^1$, $R^2$, $R^6$ and X have the same meanings as in formula (I), with a thiophosphorus compound of formula:

$$(R^3O)_2-P-SH \quad (IV)$$
$$\quad\quad\ \ \parallel$$
$$\quad\quad\ \ S$$

in which $R^3$ has the same meaning as in formula (I) .

Examples of epoxides or episulphides of formula (III) which may be mentioned in particular are:

glycidyl acrylate and glycidyl methacrylate,
thioglycidyl acrylate and thioglycidyl methacrylate (disclosed in U.S. Pat. No. 3,404,158) and
epoxy (meth)acrylates chosen from 2-epoxyethylbicyclo[2.2.1]hept-5(6)-yl (meth)acrylate, epoxydicyclopentyloxyethyl acrylate and those of the formula:

$$R^1\begin{matrix}\\ \\C\\ \parallel \\CH_2\end{matrix}\begin{matrix}O\\ \parallel \\C\end{matrix}\begin{matrix}\\ \\O\end{matrix}(CH_2)_n\begin{matrix}\\ \\CH\end{matrix}\begin{matrix}CH_2\\ \\ \\O\end{matrix} \quad (V)$$

in which $R^1$ is chosen from a hydrogen atom and a methyl radical and n is an integer ranging from 1 to 16, those of formula:

$$R^1\begin{matrix}\\ \\C\\ \parallel \\CH_2\end{matrix}\begin{matrix}O\\ \parallel \\C\end{matrix}\begin{matrix}\\ \\O\end{matrix}CH_2\begin{matrix}\\ \\CH\end{matrix}\begin{matrix}CHR^2\\ \\ \\O\end{matrix} \quad (VI)$$

in which $R_1$ is chosen from a hydrogen atom and a methyl radical and $R_2$ is chosen from alkyl radicals having from 1 to 12 carbon atoms and aryl radicals having from 6 to 12 carbon atoms, and those of formulae:

$$R^1\begin{matrix}\\ \\C\\ \parallel \\CH_2\end{matrix}\begin{matrix}O\\ \parallel \\C\end{matrix}\begin{matrix}\\ \\O\end{matrix}\text{—}\bigcirc\text{—}O \quad (VII)$$

and

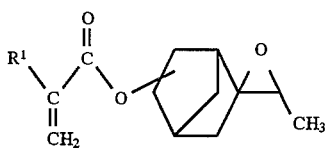

in which R¹ is chosen from a hydrogen atom and a methyl radical.

Examples of thiophosphorus compounds of formula (IV) which may be mentioned are, in particular:

those in which R³ is an alkyl radical having from 1 to 20 carbon atoms, which are well known to those skilled in the art.

those in which R³ is a $(CH_2)_p SR^4$ group, p being an integer from 2 to 12 and R⁴ being an alkyl radical having from 1 to 20 carbon atoms or a monocyclic or polycyclic cycloalkyl radical having from 4 to 10 carbon atoms, each ring in the said group comprising from 4 to 6 members. These compounds, which have not previously been disclosed, may be prepared by reaction of a sulphur-containing alcohol of formula $R^4S(CH_2)_pOH$ with phosphorus pentasulphide in accordance with the reaction:

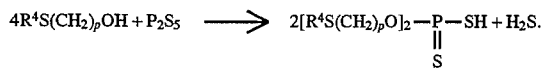

This reaction, which may be carried out in the presence of a solvent such as benzene, toluene or chloroform, is preferably carried out at a temperature of 60° C. to 110° C. approximately, without exceeding the reflux temperature when a solvent is used, and for a period of 30 minutes to 2 hours approximately.

those in which R³ is a

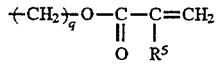

group, q being an integer ranging from 2 to 12 and R⁵ being chosen from a hydrogen atom and a methyl radical. The preparation of these compounds, which have not been disclosed hitherto, is effected by reacting an acrylic or methacrylic compound of formula:

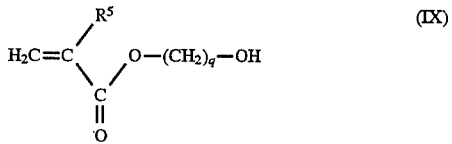

with phosphorus pentasulphide P₂S₅. This reaction is preferably carried out in the presence of a solvent such as benzene, toluene, xylenes or chloroform. The reaction is preferably carried out at a temperature of between 40° C. approximately and the reflux temperature of the solvent. The reaction time, which is variable depending on the nature of the compound of formula (IX), is generally approximately between 15 minutes and 5 hours. A proportion of 0.2 to 0.3 mol approximately of phosphorus pentasulphide per mole of compound of formula (IX) is generally used for carrying out the reaction. At the end of the reaction, the acrylic or methacrylic thiophosphorus compound of formula (IV) is isolated by treatment with an alkaline solution (sodium hydroxide for example), washing using an organic solvent and regeneration by neutralisation with a dilute inorganic acid (HCl, H₂SO₄).

Although this is not necessary, the reaction according to the invention may be carried out in the presence of a solvent or mixture of solvents such as benzene, toluene, etc. The reaction is preferably carried out at a temperature of between −10° C. and +25° C. approximately and generally using a proportion of 0.8 to 1.2 mols approximately of thiophosphorus compound per 1 mol of acrylic or methacrylic epoxide or episulphide of formula (III).

The reaction most frequently leads to the formation of a mixture of two isomers of formulae (I) and (II) in which the position of the hydroxyl or thiol group varies depending on the side at which opening of the oxirane or thiirane ring takes place. Although it of course depends on the nature of R¹, R², X, R³ and R⁶, the proportion of the isomer of formula (II) in the mixture is always very minor and is generally between 1% and 10% approximately.

Finally, a third and final subject of the present invention consists in the application of the new acrylic and methacrylic compounds described above in forming new polymers and copolymers. More precisely, the present invention relates to polymers and copolymers comprising at least one unit derived from at least one acrylic or methacrylic compound of formula (I), of formula (II) or or formula (III). (Co)polymers of this type may also comprise at least one unit derived from at least one comonomer copolymerisable with the said acrylic or methacrylic compound of formula (I), of formula (II) or of formula (III), such as, for example:

an alkyl acrylate or alkyl methacrylate in which the straight-chain or branched alkyl group, which if necessary is substituted, for example by at least one halogen atom such as chlorine or fluorine and/or by at least one hydroxyl group, possesses from 1 to 20 carbon atoms, an aryl acrylate or aryl methacrylate, such as benzyl methacrylate, a vinylaromatic hydrocarbon, such as styrene, vinyltoluene, alpha-methylstyrene, 4-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene, an unsaturated nitrile, such as acrylonitrile or methacrylonitrile, an N-substituted maleimide, such as N-ethylmaleimide, N-isopropylmaleimide, N-n-butylmaleimide, N-isobutylmaleimide, N-tert-butylmaleimide, N-n-octylmaleimide, N-cyclohexylmaleimide, N-benzylmaleimide and N-phenylmalemide, an unsaturated dicarboxylic acid anhydride, such as maleic anhydride, itaconic anhydride, citraconic anhydride or tetrahydrophthalic anhydride, acrylic acid or methacrylic acid, a polyol acrylate or polyol methacrylate, such as the diacrylates and dimethacrylates of ethylene glycol, propylene glycol, 1,3-butanediol, 1,4-butanediol, 1,6-hexanediol, neopentyl glycol, 1,4-cyclohexanediol, cyclohexane-1,4-dimethanol, 2,2,4-trimethyl-1,3-pentanediol, 2-ethyl-2-methyl-1,3-propanediol, 2,2-diethyl-1,3-propanediol, diethylene glycol, dipropylene glycol, triethylene glycol, tripropylene glycol, tetraethylene glycol, tetrapropylene glycol, trimethylolethane, trimethylolpropane, glycerol and pentaerythritol, the triacrylates and trimethacrylates of trimethylolethane, trimethylolpropane, glycerol and pentaerythritol, the tetraacrylates and tetramethacrylates of pentaerythritol, the di(meth)acrytates to hexa(meth)acrylates of dipentaerythritol, the poly(meth)acrylates of monoethoxylated or polyethoxylated or monopropoxylated or polypropoxylated polyols, such as the triacrylate and the trimethacrylate of triethorylated trimethylolpropane and tripropoxylated trimethylolpropane; the triacrylate and the trimethacrylate of tripropoxylated glycerol; and the triacrylate, trimethacrylate, tetraacrylate and tetramethacrylate of tetraethoxylated pentaerythritol, an epoxy acrylate or methacrylate chosen from 2-epoxyethylbicyclo[2.2.1]hept-5(6)-yl (meth)acrylate, epoxydicyclopentyloxyethyl acrylate and those of formulae (V), (VI), (VII) and (VIII) described above, oxazolidones chosen from those of formula:

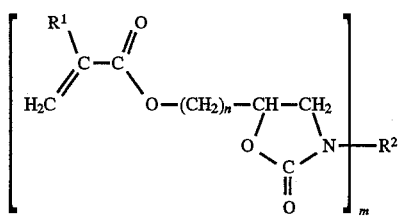
(X)

and those of formula:

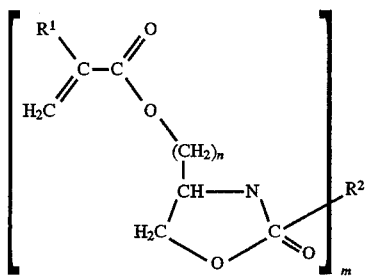
(XI)

in which formulae:

$R^1$ is chosen from a hydrogen atom and a methyl radical,
n is an integer ranging from 1 to 12,
m is an integer ranging from 1 to 3,
$R^2$ is a straight-chain, branched or cyclic alkyl or aromatic hydrocarbon radical having from 5 to 12 carbon atoms, acrylic and methacrylic compounds chosen from those of formula:

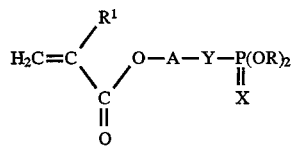
(XII)

in which:

$R^1$ is chosen from a hydrogen atom and a methyl radical,
A is chosen from $(CH_2)_n$ radicals, for which n is an integer from 2 to 12, and the $—(CH_2CH_2O)_d—CH_2CH_2—$radical, d being an integer ranging from 1 to 20,
X is chosen from sulphur and oxygen atoms,
Y is chosen from sulphur and oxygen atoms, on condition that X is a sulphur atom and Y is an oxygen atom if A is the $—(CH_2CH_2O)_d—CH_2CH_2—$ radical, and
R is chosen from alkyl radicals having from 1 to 20 carbon atoms and $—(CH_2)_pSR^3$ groups in which p is an integer ranging from 3 to 12 and $R^3$ is an alkyl radical having from 1 to 20 carbon atoms, those of formula:

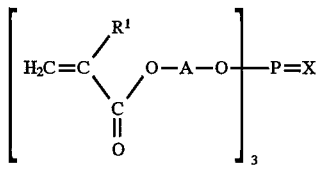

in which:

$R^1$ is chosen from a hydrogen atom and a methyl radical,
A is chosen from $(CH_2)_n$ radicals for which n is an integer from 2 to 12 and the $—(CH_2CH_2O)_d—CH_2CH_2$-radical, d being an integer ranging from 1 to 20, and
X is chosen from sulphur and oxygen atoms, and those of formula:

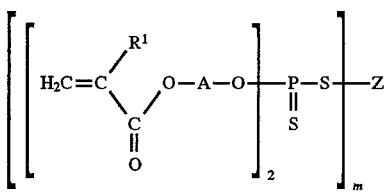

in which:

$R^1$ is chosen from a hydrogen atom and a methyl radical,
A is chosen from $(CH_2)_n$ radicals for which n is an integer from 2 to 12,
m is an integer ranging from 1 to 3, and
Z is chosen from a hydrogen atom, $R^2QH$ radicals, $R^2$ being an alkyl radical having from 2 to 12 carbon atoms and Q being chosen from oxygen and sulphur atoms and the atoms of the metals of groups IA, IIA, IIIA, IB, IIB, VIB, VIIB and VIII of the Periodic Classification, on condition that Z is chosen from a hydrogen atom and the $R^2OH$ radicals when m is 1 and that m is the valency of Z when Z is a metal. Compounds of this type may be prepared by reaction of an acrylic or methacrylic compound of formula:

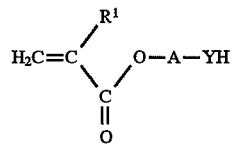
(XII)

in which $R^1$, A and Y have the same meanings as in formula (I), with a pentavalent phosphorus compound, which latter compound may be, for example, a compound of formula $PXT_3$ in which X has the same meaning as in formula (II) and T denotes a halogen atom, or a phosphorus compound of formula:

(XII)

in which R and X have the same meanings as in formula (I) and T denotes a halogen atom, or the pentasulphide $P_2S_5$.

an acrylamide or methacrylamide or a dialkylaminoalkylacrylate or methacrylate and their quaternary salts, and
2-(2-norbornyloxy) ethyl acrylate and methacrylate and 2-(2-dimethanodecahydronaphthyloxy) ethyl acrylate and methacrylate.

Polymers and copolymers of this type are obtained by (co)polymerising at least one acrylic or methacrylic compound of formula (I) or of formula (II) and, if necessary, at least one copolymerisable comonomer, such as defined above, in the presence of at least one free radical initiator such as a peroxide, a hydroperoxide or a diazo compound. The (co)polymerisation is generally carried out at a temperature of between 50° C. and 120° C. approximately and using one of the monomers as solvent. It may also take place in emulsion in water, at temperature of between 50° C. approximately and 100° C., in the presence of at least one surfactant.

The polymers of this invention can be used in the same conventional manner as other acrylic and methacrylic polymers, e.g., formed into molded, cast, and extruded articles, coating materials, etc.

(In the above description and throughout the specification and claims, the numerical range of "from x to y", x and y being integers, is intended to include both x and y.)

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited above and below, and of corresponding French Application 2,663,334, filed Jun. 14, 1990, are hereby incorporated by reference.

EXAMPLES 1 TO 4

12 millimoles of a sulphur-containing alcohol of formula $R^4S(CH_2)_pOH$ and 10 milliliters of benzene are introduced, under a stream of nitrogen, into a reactor fitted with a condenser, a thermometer and a dropping funnel and provided with a magnetic stirrer. The mixture is heated to reflux and 6 millimoles of phosphorus pentasulphide are then introduced in fractions and heating under reflux is continued for 1 hour. After returning to ambient temperature, the solvent is removed with the aid of a rotary evaporator. A colourless liquid is thus collected, in a yield higher than 95%, and this is then characterised by proton nuclear magnetic resonance using a JEOL PMX60 Si spectrometer. All of the spectra obtained contain a chemical shift at 4.2 ppm (m, 4H). They also contain chemical shifts (expressed in ppm) which vary from one product to another and the characteristics of which are mentioned in Table I below as a function of the value of p and the meaning of $R^4$. The reaction products are also characterised by phosphorus 31 nuclear magnetic resonance (NMR) using a Brucker 80 MHz spectrometer. The spectra are recorded with proton decoupling, the reference being phosphoric acid $H_3PO_4$. The chemical shifts (expressed in ppm) are shown in Table I below.

TABLE I

| Ex. | $R^4$ | P | δ(SH) | δ(CH$_2$S) | δ(CH$_2$) | δ(CH$_3$) | $^{31}P$ NMR |
|---|---|---|---|---|---|---|---|
| 1 | C(CH$_3$)$_3$ | 3 | 3.4s | 2.6(t, 4H) | 2.0(m, 4H) | 1.3 (s, 18H) | 85.9 |

TABLE I-continued

| Ex. | $R^4$ | P | δ(SH) | δ(CH$_2$S) | δ(CH$_2$) | δ(CH$_3$) | $^{31}P$ NMR |
|---|---|---|---|---|---|---|---|
| 2 | C(CH$_3$)$_3$ | 5 | 3.6s | 2.6(t, 4H) | 1.6(m, 8H) 1.5(m, 4H) | 1.3 (s, 18H) | 85.6 |
| 3 | cyclo-hexyl | 3 | 3.4s | 2.7(m, 6H) | 1.3 to 2.2 (m, 24H) | | 85.5 |
| 4 | cyclo hexyl | 6 | 3.5s | 2.6(m, 6H) | 1.3 to 2.2 (m, 36H) | | 85.3 |

The sulphur-containing dithiophosphoric acids obtained are also characterised by carbon 13 nuclear magnetic resonance using a Brucker 80MHz spectrometer by reference to tetramethylsilane and with proton decoupling but without phosphorus decoupling. The spectra obtained contain the chemical shifts (expressed in ppm) indicated in Table II below.

TABLE II

| Ex. | δ(C—O) | δ(CH$_2$) | δ(C—S) | δ(C) | δ(CH$_3$) |
|---|---|---|---|---|---|
| 1 | 67.2 66.9 d; J(PC) J=6, 1Hz | 30.4 30.0 d; J(PC) J=8, 5Hz | 24.3 | 42.1 | 30.9 |
| 2 | 68.1 67.8 d; J(PC) J=6, 1Hz | 29.6 29.2 27.9 | 25.0 | 41.7 | 30.9 |

EXAMPLES 5 TO 7

12 millimoles of hydroxylated methacrylate of formula (IX) (where $R^5$=methyl radical) and 10 milliliters of benzene are introduced, under a stream of nitrogen, into a reactor fitted with a condenser, a thermometer and a dropping funnel and provided with a magnetic stirrer. The mixture is heated to reflux and 6 millimoles of phosphorus pentasulphide are then introduced in fractions. Heating under reflux is continued until all of the phosphorus pentasulphide has disappeared. After returning to ambient temperature, the solvent is removed with the aid of a rotary evaporator. A colourless liquid is thus collected, in a yield higher than 95%, which will be kept at a temperature of 0° C. until any subsequent use. The methacrylic dithiophosphoric acids obtained are then characterised by proton nuclear magnetic resonance using a JEOL PMX 60 SI spectrometer. All of the spectra obtained contain chemical shifts at 6.1 ppm (m, 2H), 5.6 ppm (m, 2H), 4.3 ppm (m, 8H), 3.2 ppm (s) and 2.0 ppm (m, 6H). They also contain a chemical shift (expressed in ppm) which varies from one product to another and the characteristics of which are mentioned in Table III below as a function of the value of q in the formula (VII).

TABLE III

| Example | 5 | 6 | 7 |
|---|---|---|---|
| q | 2 | 3 | 6 |
| δ (CH$_2$) | | 2.1(m, 4H) | 2.0(m, 16H) |

EXAMPLES 8 TO 20

10 millimoles of a dithiophosphoric acid are introduced into a reactor fitted with a condenser, a thermometer and a dropping funnel and provided with a magnetic stirrer. The reactor is placed at 0° C. and 10 millimoles of (meth)acrylic oxirane or thiirane are then added dropwise. After the end of the addition, stirring is continued for 10 minutes at 0° C. and then for 2 hours at 23° C. A colourless oil is then collected, in a yield higher than 95%, and is characterised by:

phosphorus 31 nuclear magnetic resonance (NMR) in accordance with the method described for Examples 1 to 4. The chemical shift (expressed in ppm) recorded for each spectrum will be found in Table IV below;

proton nuclear magnetic resonance (NMR) using a JEOL PMX 60 Si spectrometer. The spectra contain the chemical shifts (expressed in ppm) indicated in Table IV below.

The oxirane—or the thiirane—used is glycidyl acrylate (Examples 8 and 9), glycidyl methacrylate (Examples 10 to 16) and then thioglycidyl methacrylate (Examples 17 to 20). The dithiophosphoric acid used corresponds to formula (IV), $R^3$ being an alkyl or aryl radical (Examples 8, 10, 11, 12 and 17) or a $(CH_2)_p SR^4$ group, the value of p and the nature of $R^3$ and $R^4$ being specified in Table IV.

TABLE IV

| | Example | | | | |
|---|---|---|---|---|---|
| | 8 | 9 | 10 | 11 | 12 |
| $R^3$ | $CH(CH_3)_2$ | | $C_2H_5$ | $CH(CH_3)_2$ | $C_6H_5$ |
| p | | 3 | | | |
| $R^4$ | | cyclohexyl | | | |
| $\delta(CH=)$ | 5.9(m, 1H) | 5.9(m, 1H) | 5.6(m, 1H) | 5.6(m, 1H) | 5.6(m, 1H) |
| | 6.2(m, 1H) | 6.2(m, 1H) | 6.1(m, 1H) | 6.1(m, 1H) | 6.1(m, 1H) |
| | 6.4(m, 1H) | 6.4(m, 1H) | | | |
| $\delta(CH_2—O)$ | 4.9(m, 2H) | 4.3(m, 7H) | 4.3(m, 7H) | 4.9(m, 2H) | 4.2(m, 3H) |
| | 4.3(m, 3H) | | | 4.3(m, 3H) | |
| $\delta(OH)$ | 2.8s | 2.7s | 2.8s | 2.8s | 2.9s |
| $\delta(CH_2—S)$ | 2.7 to 3.3 | 2.7 to 3.3 | 2.8 to 3.4 | 2.8 to 3.4 | 2.8 to 3.4 |
| | (m, 2H) | (m, 2H) | (m, 2H) | (m, 2H) | (m, 2H) |
| | | 2.6(m, 6H) | | | |
| $\delta(CH_2)$ | | 1.2 to 2.2 | | | |
| | | (m, 24H) | | | |
| $\delta(CH_3)$ | 1.4(d, 12H) | | 2.0(m, 3H) | 2.0(m, 3H) | 2.0(m, 3H) |
| | | | 1.4(t, 6H) | 1.3(d, 12H) | |
| $\delta(^{31}P\ NMR)$ | 91.7 | 96.2 | 94.8 | 91.7 | 91.3 |

| | Example | | | |
|---|---|---|---|---|
| | 13 | 14 | 15 | 16 |
| p | 3 | 5 | 3 | 6 |
| $R^4$ | $C(CH_3)_3$ | $C(CH_3)_3$ | Cyclohexyl | Cyclohexyl |
| $\delta(CH_2=)$ | 5.6(m, 1H) | 5.6(m, 1H) | 5.6(m, 1H) | 5.6(m, 1H) |
| | 6.1(m, 1H) | 6.1(m, 1H) | 6.1(m, 1H) | 6.1(m, 1H) |
| $\delta(CH_2—O)$ | 4.2(m, 7H) | 4.2(m, 7H) | 4.3(m, 7H) | 4.3(m, 7H) |
| $\delta(OH)$ | 2.6s | 2.7s | 3.0s | 3.0s |
| $\delta(CH_2—S)$ | 2.7 to 3.3 | 2.7 to 3.3 | 2.8 to 3.3 | 2.8 to 3.3 |
| | (m, 2H) | (m, 2H) | (m, 2H) | (m, 2H) |
| | | | 2.6(m, 6H) | 2.6(m, 6H) |
| $\delta(CH_2)$ | 2.0(m, 4H) | 1.5 to 2.0 | 1.3 to 2.2 | 1.3 to 2.2 |
| | | (m, 12H) | (m, 24H) | (m, 36H) |
| $\delta(CH_3)$ | 2.0(m, 3H) | 2.0(m, 3H) | 2.0(m, 3H) | 2.0(m, 3H) |
| | 1.3(s, 18H) | 1.3(s, 18H) | | |
| $\delta(^{31}P\ NMR)$ | 96.2 | 95.5 | 96.2 | 96.3 |

| | Example | | | |
|---|---|---|---|---|
| | 17 | 18 | 19 | 20 |
| $R^3$ | $C_2H_5$ | | | |
| p | | 3 | 3 | 6 |
| $R^4$ | | $C(CH_3)_3$ | Cyclohexyl | Cyclohexyl |
| $\delta(CH_2=)$ | 5.6(m, 1H) | 5.6(m, 1H) | 5.6(m, 1H) | 5.6(m, 1H) |
| | 6.1(m, 1H) | 6.1(m, 1H) | 6.1(m, 1H) | 6.1(m, 1H) |
| $\delta(CH_2O)$ | 4.3(m, 6H) | 4.2(m, 6H) | 4.2(m, 6H) | 4.3(m, 6H) |
| $\delta(SH)$ | 2.6s | 2.5s | 2.5s | 2.6s |
| $\delta(CH_2—S)$ | 2.9 to 3.4 | 2.7 to 3.4 | 2.8 to 3.4 | 2.8 to 3.3 |
| | (m, 3H) | (m, 7H) | (m, 9H) | (m, 9H) |
| $\delta(CH_2)$ | | 2.0(m, 4H) | 1.3 to 2.2 | 1.3 to 2.2 |
| | | (m, 12H) | (m, 24H) | (m, 36H) |
| $\delta(CH_3)$ | 2.0(m, 3H) | 2.0(m, 3H) | 2.0(m, 3H) | 2.0(m, 3H) |
| | 1.4(s, 6H) | 1.3(s, 18H) | | |
| $\delta(^{31}P\ NMR)$ | 94.5 | 95.3 | 95.2 | 95.5 |

EXAMPLE 21

Repeating the method of Examples 8 to 20, glycidyl methacrylate is reacted with the dithiophosphoric acid of formula:

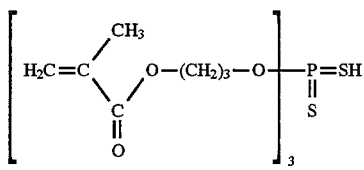

the latter being obtained by reaction between 0.12 mol of 3-hydroxypropyl methacrylate and 0.03 mol of phosphorus pentasulphide at 80° C. for 30 minutes and in 100 ml of benzene.

The reaction leads to the formation, in a yield higher than 95%, of a pale yellow liquid, the analysis of which by nuclear magnetic resonance reveals the presence of a mixture of the isomers

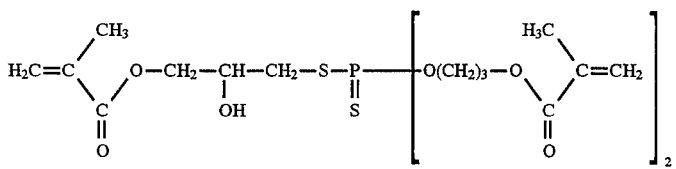

and

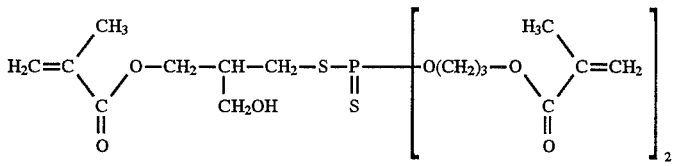

Polymers and copolymers can be made from any and all of the monomers produced in the above examples.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the preparation of an acrylic or methacrylic compound of the formula:

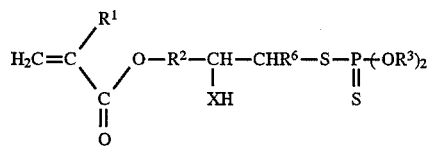

or of the formula:

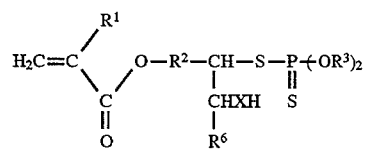

in which formulae:

$R^1$ is chosen from a hydrogen atom and a methyl radical,

X is a hetero atom chosen form oxygen and sulphur, $R^2$ is chosen from straight-chain or branched alkylene groups, monocyclic or polycyclic cycloalkylene, alkylarylene or arylalkylene groups comprising from 1 to 12 carbon atoms, $R^6$ is chosen from a hydrogen atom and alkyl and aryl radicals having from 1 to 12 carbon atoms, and $R^3$ is chosen from alkyl and aryl radicals having from 1 to 20 carbon atoms, $-(CH_2)_pSR^4$ groups in which p is an integer ranging from 2 to 12 and $R^4$ is an alkyl radical having from 1 to 20 carbon atoms, or a monocyclic or polycyclic cycloalkyl group having 4 to 10 carbon atoms, each ring in said group having 4 to 6 carbon atoms, and

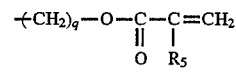

groups in which q is an integer ranging from 2 to 12 and $R^5$ is chosen from a hydrogen atom and a methyl radical, comprising reacting an acrylic or methacrylic epoxide or episulphide of formula:

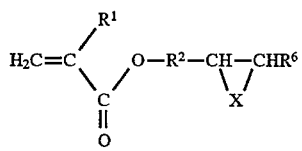

in which $R^1$, $R^2$, $R^6$ and X have the same meanings as in formula (I), with a thiophosphorus compound of formula:

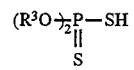

in which $R^3$ has the same meaning as in formula (I).

2. A preparation process according to claim 1, wherein the reaction is carried out at a temperature of between −10° C. and +25° C.

3. A preparation process according to claim 1, wherein the reaction is carried out using a proportion of 0.8 to 1.2 moles of thiophosphorus compound per 1 mol of acrylic or methacrylic epoxide or episulphide.

4. A preparation process according to claim 2, wherein the reaction is carried out using a proportion of 0.8 to 1.2 moles of thiophosphorus compound per 1 mole of acrylic or methacrylic epoxide or episulfide.

5. A process according to claim 1, wherein the epoxide or episulphide of formula (III) is:

glycidyl acrylate or glycidyl methacrylate,
thioglycidyl acrylate or thioglycidyl methacrylate, or
an epoxy (meth)acrylate which is 2-epoxyethyl-bicyclo[2.2.1]hept-5(6)-yl (meth)acrylate, epoxydicyclopentyloxyethyl acrylate,

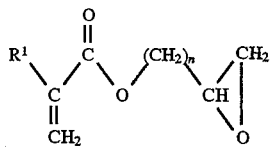
(V)

in which $R^1$ is hydrogen or methyl, and n is an integer ranging from 1 to 16,

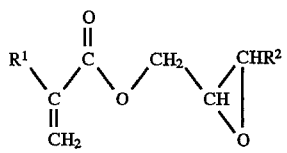
(VI)

in which $R^1$ is hydrogen or methyl, and $R^2$ is an alkyl radical having from 1 to 12 carbon atoms or an aryl radical having from 6 to 12 carbon atoms,

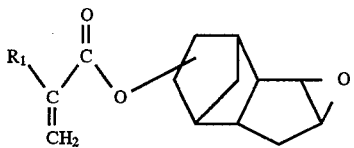
(VII)

or

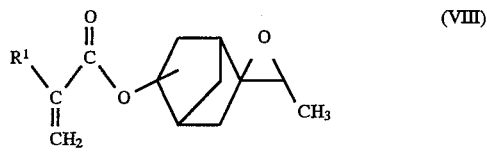
(VIII)

in which $R_1$ is hydrogen or methyl.

6. A process according to claim 1, wherein in the thiophosphorus compound of formula (IV) $R^3$ is an alkyl radical having from 1 to 20 carbon atoms.

7. A process according to claim 1, wherein in the thiophosphorus compound of formula IV, $R^3$ is a $(CH_2)_p SR^4$ group, p being an integer from 2 to 12 and $R^4$ being an alkyl radical having from 1 to 20 carbon atoms or a monocyclic or polycyclic cycloalkyl radical having from 4 to 10 carbon atoms, each ring in said group having from 4 to 6 atoms.

8. A process according to claim 1, wherein in the thiophosphorus compound of formula IV, $R^3$ is a

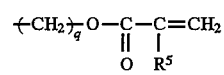

group, q being an integer ranging from 2 to 12 and $R^5$ being hydrogen or methyl.

* * * * *